US006447458B1

(12) United States Patent
Farrell et al.

(10) Patent No.: US 6,447,458 B1
(45) Date of Patent: Sep. 10, 2002

(54) METHOD AND SYSTEM OF COLOR CODING COMPONENTS OF CENTRAL VENOUS AND PULMONARY ARTERY WEDGE PRESSURE WAVEFORMS

(75) Inventors: Robert Michael Farrell, Brown Deer, WI (US); Claudio P. Mejia, Stafford, TX (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/681,538

(22) Filed: Apr. 25, 2001

(51) Int. Cl.[7] ............................. A61B 5/02; A61B 5/04
(52) U.S. Cl. ................... 600/500; 600/501; 600/485; 600/509; 600/521
(58) Field of Search ................... 600/500, 502, 600/501, 485, 486, 508, 509, 519, 521

(56) References Cited

U.S. PATENT DOCUMENTS

| 4,907,596 | A | * | 3/1990 | Schmid et al. | 600/485 |
|---|---|---|---|---|---|
| 5,033,472 | A | * | 7/1991 | Sato et al. | 600/504 |
| 5,178,154 | A | * | 1/1993 | Ackmann et al. | 600/526 |
| 5,634,467 | A | * | 6/1997 | Nevo | 600/490 |
| 5,833,619 | A | * | 11/1998 | Freed et al. | 600/485 |
| 5,921,936 | A | * | 7/1999 | Inukai et al. | 600/490 |
| 6,083,171 | A | * | 7/2000 | Ono et al. | 600/494 |

* cited by examiner

Primary Examiner—Kevin Shaver
Assistant Examiner—Navin Natnithithadha
(74) Attorney, Agent, or Firm—Michael Best & Friedenrich LLP (57) ABSTRACT

A method and system for identifying components of a waveform. The system includes an ECG acquisition module, a pressure waveform acquisition module to acquire a pressure waveform, and an analysis module coupled to the ECG acquisition module and the pressure waveform acquisition module. A monitor or similar display device is coupled to the analysis module. The analysis module is operable to determine three peaks in the pressure waveform corresponding to "a", "c", and "v" waves. Those "a", "c", or "v" waves that are identified by the analysis module are displayed on a monitor or similar device such that they are distinguished from each other and the remainder of the displayed waveform. The method involves displaying a waveform; identifying a number of peaks in a number of intervals of the waveform, and modifying the displayed waveform such that the identified peaks are distinguished from each other and the rest of the pressure waveform.

28 Claims, 5 Drawing Sheets

METHOD AND SYSTEM OF COLOR CODING COMPONENTS OF CENTRAL VENOUS AND PULMONARY ARTERY WEDGE PRESSURE WAVEFORMS

BACKGROUND OF INVENTION

The present invention relates to methods and devices used to measure and record physiological data, such as blood pressure and electrocardiogram data. More particularly, the invention relates to a method and a system of distinguishing components of physiological activity waveforms.

Modern medical practice involves monitoring a variety of physiological data, including electrical activity and blood pressure. Electrocardiograms (ECG) are used to measure electrical activity that controls the contraction of the heart. As is known, prominent parts of an ECG are the P wave, a deflection caused by the current originating in the atrium; the QRS complex, which represents the electrical activity of the ventricles as they contract; and the T wave, which denotes ventricular relaxation. These changes in electrical activity may, in general, be sensed using electrodes attached to the body.

The pulsatile pressure of blood in the circulation system may be measured in a variety of ways and provides different information depending on where the pressure is measured. For example, central venous pressure (CVP) or right atrial pressure (RAP) measurement provides useful information about cardiovascular status and right ventricular function. Frequently, CVP and RAP measurements are used to monitor the volemic state and right heart function.

Figure 1:
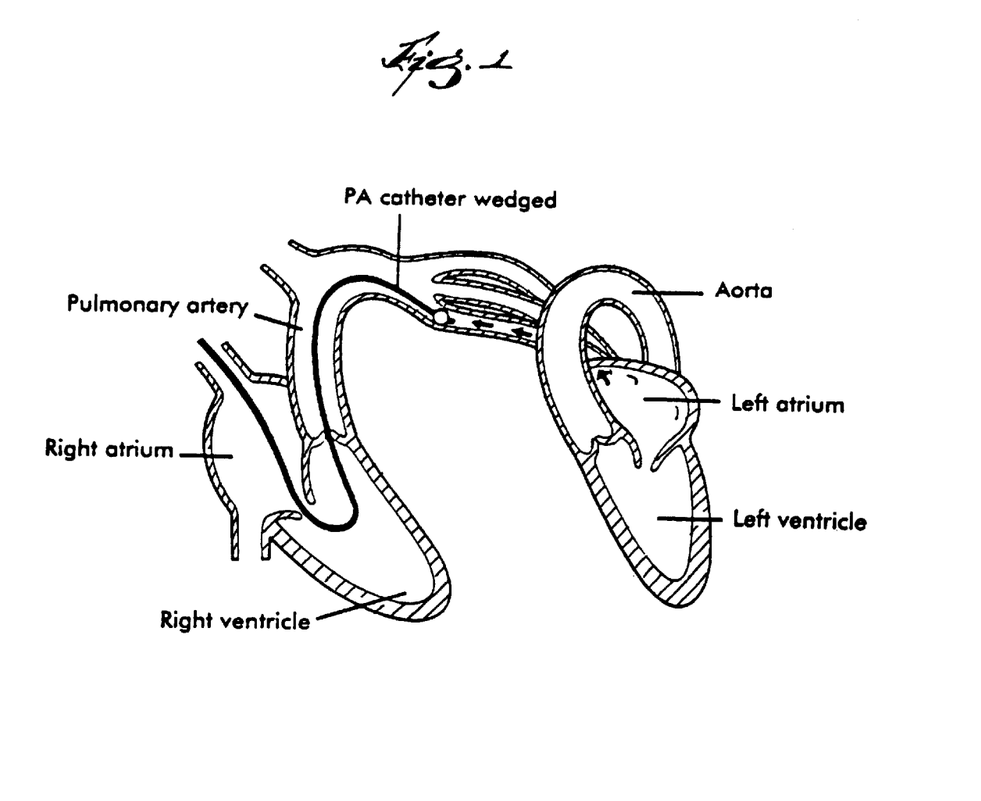
FIG. 1 is an illustration of PAWP measurement.

"Pulmonary artery pressure monitoring provides additional information about heart function. One measurement that may be made with a pulmonary artery catheter is the pulmonary artery wedge pressure (PAWP). In this measurement, a balloon near the end of the catheter is inflated, occluding flow through that branch of the pulmonary circulation (as shown in FIG. 1). When so positioned, the balloon is said to be wedged in the pulmonary artery. The stagnant blood at the distal tip of the catheter is, in effect, at the same pressure as the blood in the left atrium, which, when the mitral valve is open, is also at the same pressure as the blood in the left ventricle. During the PAWP measurement, the pulmonary artery waveform takes on a dampened appearance, because the pressure waveform represents the left atrial pressure rather than the pulsatile pulmonary artery pressure. Prominent parts of the PAWP waveform may be identified and correlated to the subject's ECG. An "a" wave is produced by left atrial contraction and follows the P wave of the ECG. The descending portion of the "a" wave is called the x-descent, reflecting left atrial relaxation. A small positive deflection is sometimes visible on the x-descent. This deflection, called the "c" wave, is produced by the closure of the mitral valve. The "v" wave is produced by the filling of the left atrium against the closed mitral valve during ventricular systole and, therefore, occurs after the R wave of the ECG (more precisely, it occurs after the T wave of the ECG). The downstroke following the peak of the "v" wave is termed the y-descent, which represents the opening of the mitral valve and a decrease in left atrial pressure and volume during passive emptying into the left ventricle."

Figure 2:
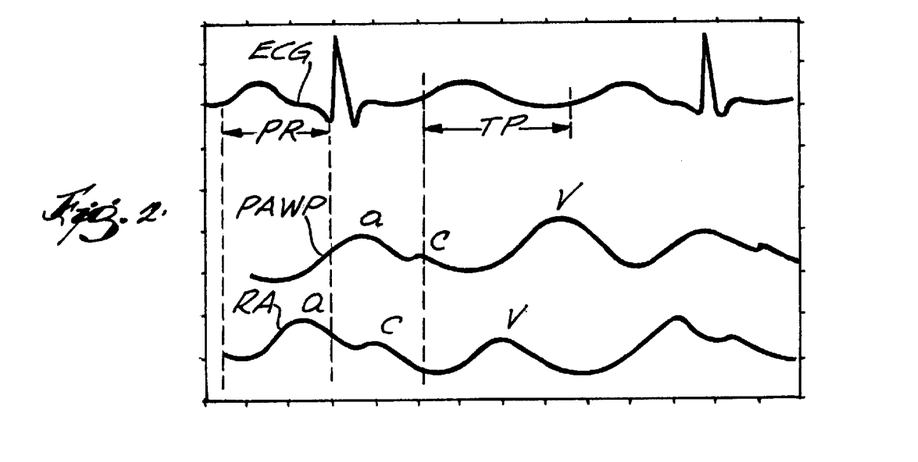
FIG. 2 is an illustration of exemplary ECG, RAP, and PAWP waveforms.

Because the PA catheter is in effect sensing the pressure of the left atrium during the wedge pressure measurement, the PAWP provides the same information about left heart function as RAP measurements provide about right heart function. Thus, the morphology of the RAP and PAWP waveforms is similar, the only difference being in origin: the components of the RAP waveform are due to right heart activity, while the PAWP components are due to left heart activity. Like a PAWP waveform, a RAP waveform also has "a", "c", and "v" waves. FIG. 2 illustrates exemplary ECG, RAP, and PAWP waveforms.

"Because of the time required for the mechanical event to reach the sensing device, the "a" wave in a RAP waveform is generally observed about 80–100 msec after the P wave in an ECG. The "a" wave in a PAWP waveform is generally observed about 200–240 msec after the P wave. As noted, the decline in pressure that immediately follows the "a" wave is termed the x-descent and reflects atrial relaxation (right atrium for RAP, left for PAWP). The "c" wave is a minor wave that may appear as a distinct wave or as a notch on the "a" wave, or may be absent altogether. It reflects a slight increase in pressure in the atrium produced by closure of the valve (tricuspid valve for RAP, mitral valve for PAWP). The time difference between the "a" and "c" waves approximates the PR interval of the ECG waveform. The "v" wave is generally observed near the end of the T wave of the ECG waveform in the RAP waveform or during the TP interval in the PAWP waveform. The y-descent is produced by the opening of the valve (tricuspid valve for RAP, mitral valve for PAWP)."

"Normal mean pressure values are 2–6 mmHg for RAP and 4–12 mmHg for PAWP. Under normal (nonpathologic) conditions, the "a" and "v" waves are small and of approximately equal amplitude. Instances in which either the "a" or "v" wave is elevated more than 2 or 3 mmHg above the other wave are indicative of valvular pathologies or ventricular failure. Although it is known that detecting and measuring "a", "c", and "v" waves provides useful information like that just noted, detecting and measuring these waveform components is not an easy task, particularly when reviewing waveforms on a monitor screen. In fact, the usual practice is to print a strip recording of pressure and simultaneous ECG waveforms and, using a straight edge, line up the electrical events with the mechanical (pressure) events. Complicating things further, there are circumstances caused by a patient's medical condition where it is difficult to differentiate large "v" waves from regular pulmonary artery pressure pulses on the pressure tracing."

SUMMARY OF INVENTION

Accordingly, there is a need for an improved method and system that identifies components of pressure waveforms. In particular, there is a need for a method and system that assists clinicians in identifying pressure waveform components on a monitor screen.

In one embodiment, the invention provides a system that identifies components of a waveform. The system includes an ECG acquisition module, a pressure waveform acquisition module to acquire a pressure waveform, and an analysis module coupled to the ECG acquisition module and the pressure waveform acquisition module. A monitor or similar display device is coupled to the analysis module.

The analysis module establishes a time reference based on R waves in an ECG, determines a first interval in the pressure waveform between a first point offset a predetermined amount ahead of a first R wave and a second point offset a predetermined amount behind the first R wave. The analysis module also identifies the highest peak of the pressure waveform in the first interval, identifies a second R wave in the ECG subsequent in time to the first R wave, establishes a second interval that extends from the second point to a third point, where the third point is positioned at a distance ahead of the second point equal to a first percentage of the interval from the second point to a predetermined amount behind the second R wave. The analysis module also identifies the highest peak in the pressure waveform in the second interval, establishes a third interval that extends from the highest peak in the first interval to a fourth point positioned at a distance ahead of the highest peak in the first interval equal to a second percentage of the distance between the highest peak in the first interval and the highest peak in the second interval, and identifies the highest peak in the pressure waveform in the third interval.

After identifying the peaks, the analysis module generates an output signal that causes a monitor to display a waveform representing the pressure waveform such that the identified highest peaks of the pressure waveform in the first, second, and third intervals are distinguished from each other and the rest of the displayed waveform.

In another embodiment the invention provides a method of identifying waves in a pressure waveform. The method includes displaying the waveform; establishing a time reference based on R waves in an ECG; determining a first interval in the pressure waveform between a first point offset a predetermined amount ahead of a first R wave and a second point offset a predetermined amount behind the first R wave; and identifying the highest peak of the pressure waveform in the first interval.

Once the highest peak of the pressure waveform in the first interval is identified, a second R wave in the ECG subsequent in time to the first R wave is identified. Following the identification of the second R wave, the method involves establishing a second interval that extends from the second point to a third point, the third point being positioned at a distance ahead of the second point equal to a first percentage of the interval from the second point to a predetermined amount behind the second R wave. The highest peak in the pressure waveform in the second interval is identified. Then a third interval is determined. The third interval extends from the highest peak in the first interval to a fourth point positioned at a distance ahead of the highest peak in the first interval equal to a second percentage of the distance between the highest peak in the first interval and the highest peak in the second interval. The method also includes identifying the highest peak in the pressure waveform in the third interval and modifying the displayed waveform such that the identified highest peaks of the pressure waveform in the first, second, and third intervals are distinguished from each other and the rest of the pressure waveform. It is preferable that the peaks be distinguished according to a color scheme.

As is apparent from the above, it is an advantage of the invention to provide a method and system of identifying pressure waveform components. Other features and advantages of the invention will become apparent by consideration of the detailed description and accompanying drawings.

DETAILED DESCRIPTION

Before embodiments of the invention are explained, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

Figure 3:
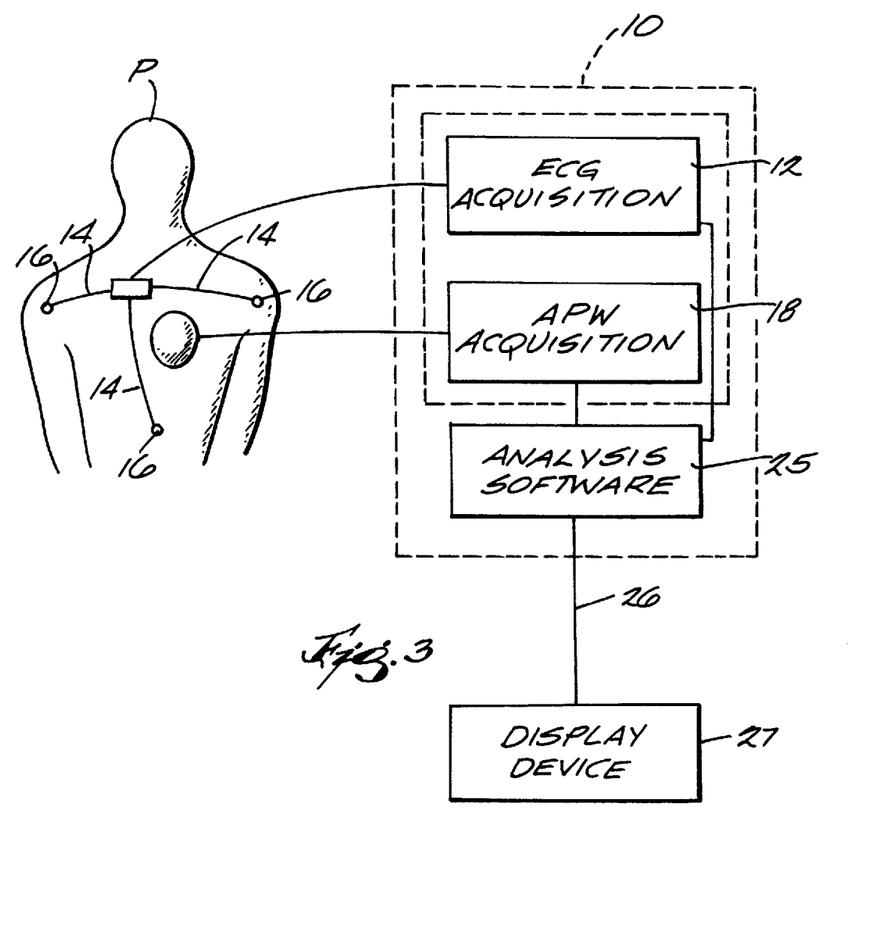
FIG. 3 is a schematic diagram of an apparatus embodying the invention.

"FIG. 3 illustrates an apparatus or device 10 for acquiring ECG and atrial pressure waveforms that embodies the invention. While this apparatus is shown as a single unit, the apparatus may be separated into discrete components that operate generally independent of the others. The apparatus includes an ECG acquisition module or circuit 12 that, in the usual application, is externally connected to a patient P through leadwires 14 and electrodes 16 attached to the patient's skin. The invention, however, is equally applicable to ECGs that are acquired in other ways, e.g., through electrodes placed directly on the heart, through transesophageal monitoring, etc."

"In the embodiment illustrated, the acquisition device 10 also includes an atrial pressure waveform acquisition module or circuit 18 (APWAC). Typically, the APWAC is connected to one or more pressure sensors or transducers (not shown) that are in turn connected to fluid-filled catheters that are positioned in the patient's heart or vena cava. For example, the acquisition circuit 18 could be coupled to a catheter positioned in the right atrium to acquire a RAP waveform and a catheter wedged in the pulmonary artery to acquire a PAWP waveform (left heart activity). It should be understood that the acquisition circuit 18 could be modified or substituted for, as needed, when analyzing other pressure phenomena including, for example, central venous pressure."

The acquisition device 10 also includes an analysis module 25 connected to the acquisition module or circuit 18 and ECG acquisition module 12. The analysis module 25 includes analysis software that provides a means for identifying at least portions of the atrial pressure waveforms acquired by the acquisition circuit 18 using the ECG waveform as a reference. The analysis module 25 generates an output signal that is delivered through a link 26 to a monitor 27 or similar display device.

Figure 4:
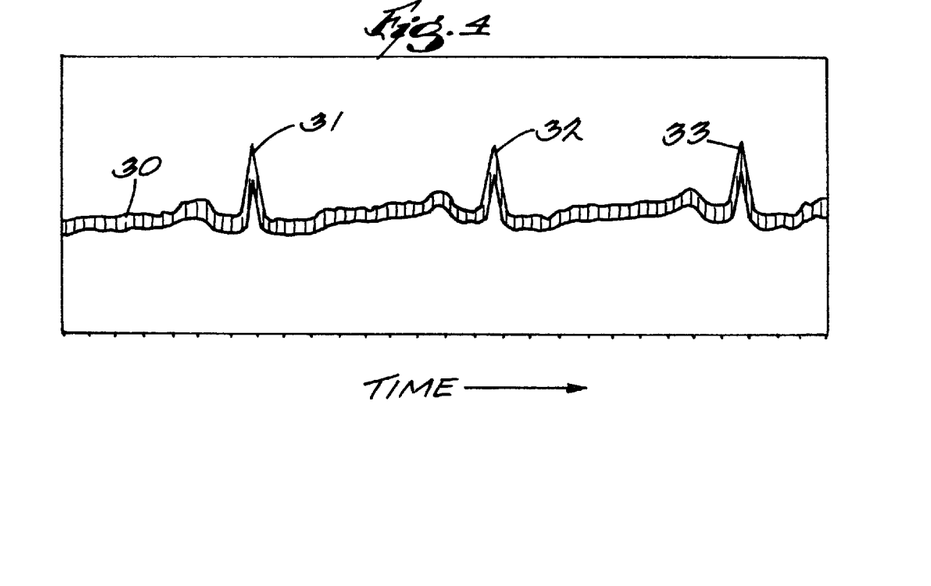
FIG. 4 is a waveform diagram of an exemplary ECG with several R waves."
Figure 5:
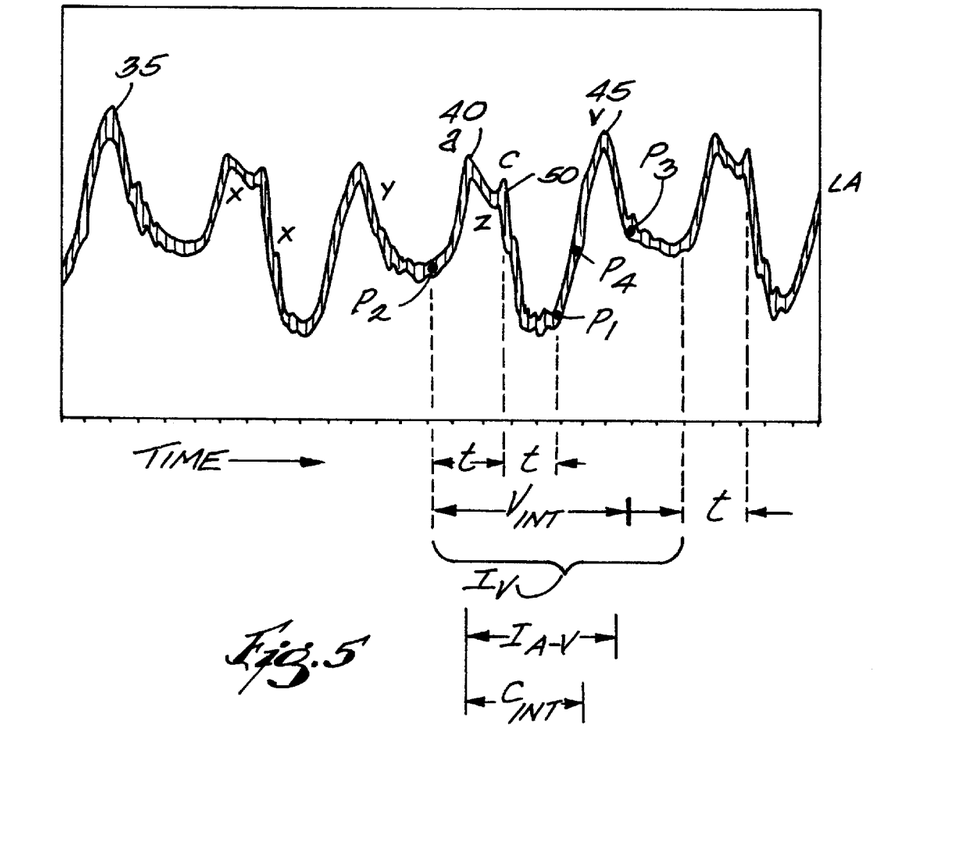
FIG. 5 is a diagram of an exemplary atrial pressure waveform.

FIG. 4 illustrates an exemplary ECG waveform 30 with three R waves 31, 32, and 33. FIG. 5 illustrates an exemplary atrial pressure waveform 35. The determination of "a", "v", and "c" waves will be explained specifically with respect to the waveform 35. However, as would be understood by those of ordinary skill in the art, the invention may be applied to the analysis of central venous pressure waveforms as well as PAWP and RAP waveforms.

"The "a", "v", and "c" waves in the waveform 35 are determined or identified using the R waves of the ECG waveform 30 as a time reference. "a" waves are found by searching for the maximum peak pressure in an interval on the pressure waveform 35 from a point P1, located t seconds to the right of the R wave 32, to a point P2, located t seconds to the left of the R wave 32. The inventor(s) has (have) found that the value of the time-offset t should be based upon the heart rate of the patient. For heart rates less than 100 BPM (beats per minute), t should be set at about 150 ms. For heart rates between 100 and 150 BPM, t should be set at about 100 ms. For heart rates of 150 BPM or greater, t should be set at 75 ms. As shown in FIG. 5, an "a" wave 40 occurs in the interval between P1 and P2."

Once the "a" wave 40 has been found, the "v" wave may be found in the waveform 35 by searching for the maximum peak in an interval $V_{INT}$. The interval $V_{INT}$ extends from point P2 to point P3. Point P3 is positioned at a distance to the right of point P2 equal to 75% of an interval $I_V$ from point P2 to t seconds to the left of the R wave 33. As shown in FIG. 5, a "v" wave 45 occurs in the interval between P2 and P3.

"The "c" wave may be found in the waveform 35 by searching for the highest peak following the "a" wave 40 in an interval $C_{INT}$. The interval $C_{INT}$ extends from about 25% to about 50% of the elapsed time (represented by an interval $I_{A-V}$) from the "a" wave 40 to the "v" wave 45 depending on the particular QRS of the reference ECG. In other words, the distance the interval $C_{INT}$ extends is dependent on the heart rate of the patient. As is known in the art, the Q of QRS refers to the ascent in the waveform before the occurrence of an R wave and the S refers to the descent in the waveform after the occurrence of an R wave. For high heart rates, the percentage of elapsed time from the "a" wave 40 to the "v" wave 45 is at the low end of the 25 to 50% range. For low heart rates, the percentage of elapsed time from the "a" wave 40 to the "v" wave 45 is at the high end of the 25 to 50% range. As can be seen by reference to FIG. 5, the highest wave in the interval $C_{INT}$ is a "c" wave 50."

Preferably, the procedure described above is implemented as software and used to analyze atrial pressure waveforms. In particular, it is envisioned that the improvements related to identifying the "c" wave in an atrial pressure waveform may be implemented in MAC-LAB Cardiac Catheterization software sold by GE Medical Systems Information Technologies, Inc.

Figure 6:
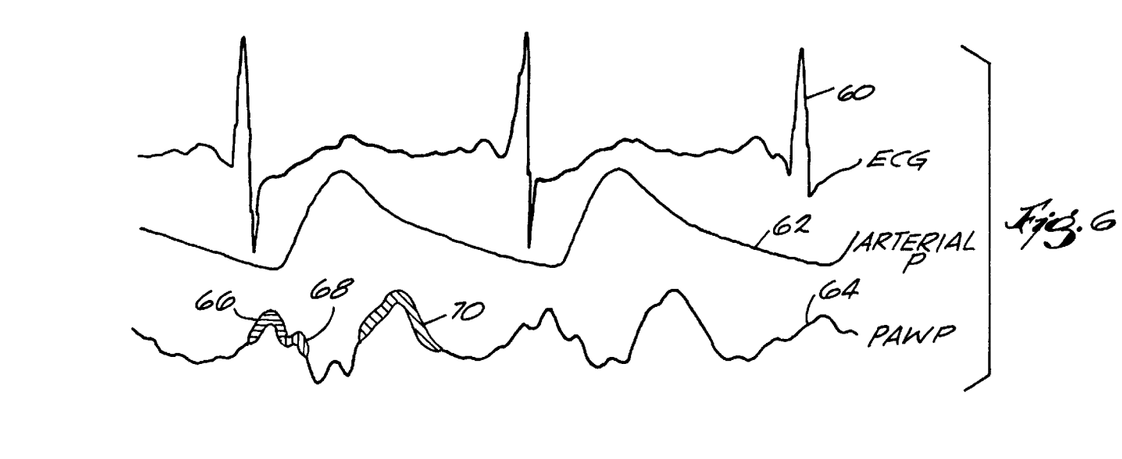
FIG. 6 is a diagram illustrating a color-coded output displayed on a monitor.
Figure 7:
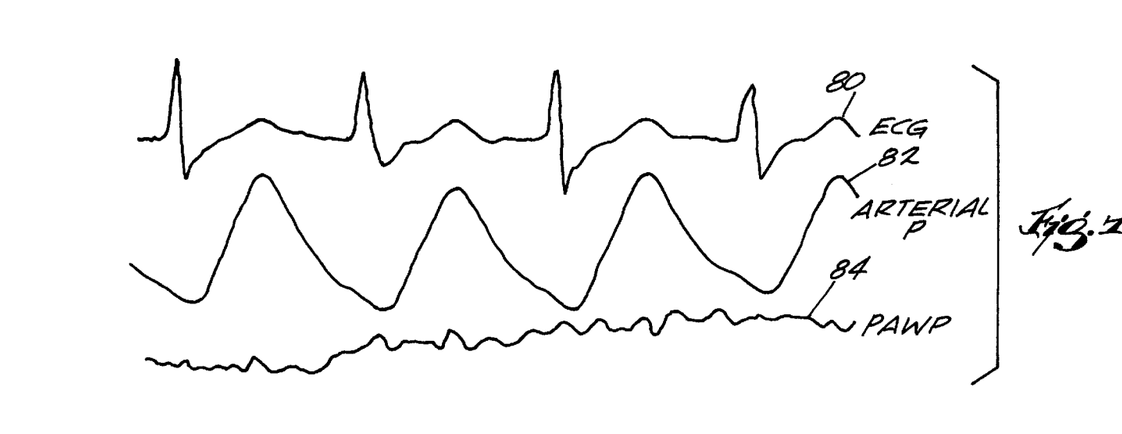
FIG. 7 is a diagram illustrating an output displayed on a monitor where the pressure waveform includes no discernable "a", "c", or "v" waves.
Figure 8:
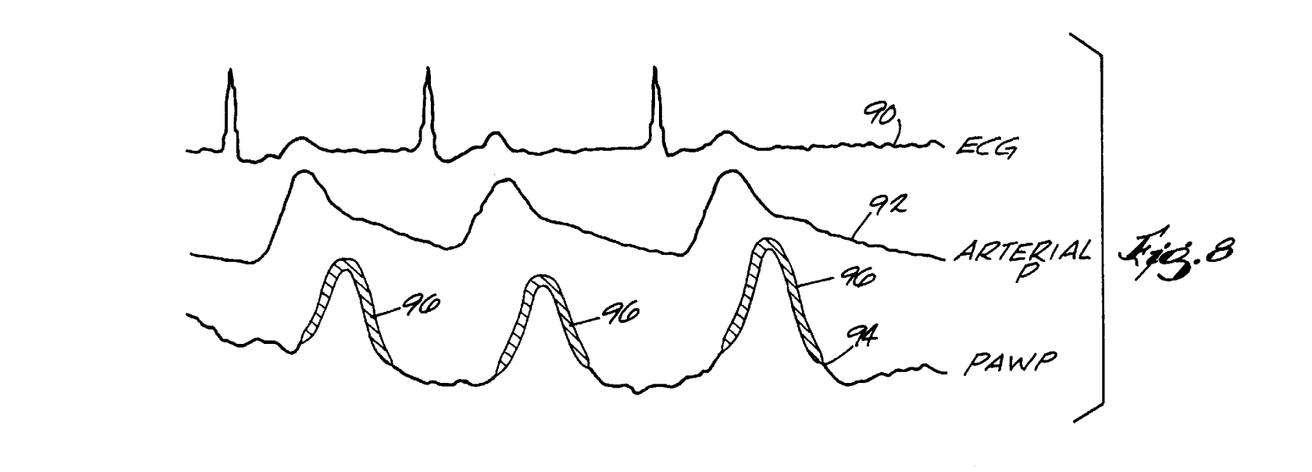
FIG. 8 is a diagram illustrating an output displayed on a monitor where the pressure waveform includes large, color-coded "v" waves.
Figure 9:
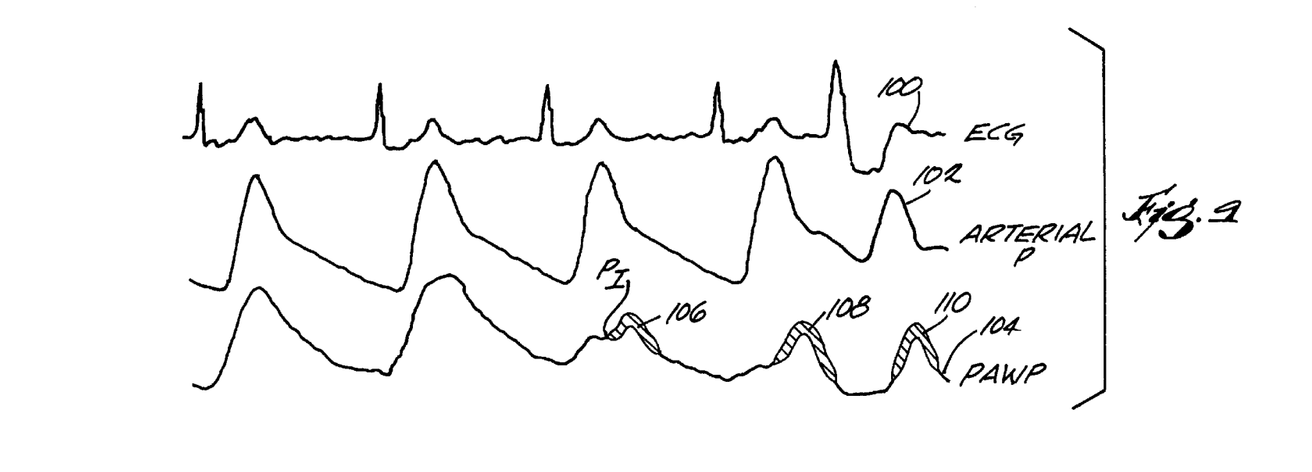
FIG. 9 is a diagram illustrating an output displayed on a monitor where the "v" waves become apparent in the pressure waveform during a wedge pressure measurement.

Once the "a", "c", and "v" waves are identified, they may be distinguished through the use of color, dashing, or the like. FIG. 6 illustrates a grouping of three waveforms; an ECG waveform 60, an arterial pressure waveform 62, and a PAWP waveform 64. The waveform 64 includes three colored sections 66, 68, and 70, corresponding to an "a" wave, a "c" wave, and a "v" wave, respectively. In the example shown, the colored sections are blue, red, and green, respectively. FIG. 7 illustrates another grouping of ECG, arterial, and PAWP waveforms 80, 82, and 84. In the example shown in FIG. 7, no discernable "a", "c", or "v" waves are present and no color coding of the waveform 84 has occurred. FIG. 8 illustrates a grouping of three ECG, arterial, and PAWP waveforms 90, 92, and 94 from a patient with severe mitral insufficiency. In this case, no "a" or "c" wave are discernable, but large "v" waves 96 are detectable and are colored green, in accordance with the color-coding scheme described above with respect to FIG. 6. FIG. 9 illustrates yet another grouping of ECG, arterial, and PAWP waveforms 100, 102, 104, respectively, that reflect physiological activity just prior to, during, and at the beginning of a wedge pressure measurement as a balloon catheter is inflated. Point $P_I$ corresponds to inflation of the balloon catheter. Upon inflation a first "v" wave 106 is discernable. Larger "v" waves 108 and 110 are apparent following inflation during the start of the PAWP measurement. Again, following the color-coding scheme above, the "v" waves are colored green.

As should be apparent, the analysis module 25 functions such that the "a", "c", and "v" waves that are identified are displayed on the monitor so that they are distinguished from each other and the remainder of the displayed waveform. The output signal of the analysis module 25 includes the information necessary to color or distinguish those sections of the waveform that correspond to an identified wave.

Thus, the invention provides, among other things, a method and system that identifies pressure waveform components. Various features and advantages of the invention are set forth in the following claims.

What is claimed is:

1. A method of identifying pressure waveform components in a pressure waveform, the method comprising:
   displaying the pressure waveform;
   establishing a time reference based on R waves in an ECG;
   determining a first interval in the pressure waveform between a first point offset a predetermined amount ahead of a first R wave and a second point offset a predetermined amount behind the first R wave;
   identifying the highest peak of the pressure waveform in the first interval;
   modifying the displayed pressure waveform such that the identified highest peak of the pressure waveform in the first interval is distinguished from the rest of the pressure waveform.

2. A method as claimed in claim 1, wherein the ECG indicates a heart rate, and wherein the offsets of the first and second points are based on the heart rate.

3. A method as claimed in claim 2, wherein the offsets of the first and second points are equal to one another.

4. A method as claimed in claim 1, further comprising
   identifying a second R wave in the ECG ahead of the first R wave;
   establishing a second interval that extends from the second point to a third point, the third point positioned at a distance ahead of the second point equal to a percentage of the interval from the second point to a predetermined amount behind the second R wave;
   identifying the highest peak in the pressure waveform in the second interval; and
   modifying the displayed waveform such that the identified highest peak of the pressure waveform in the second interval is distinguished from the highest peak in the first interval and from the rest of the pressure waveform.

5. A method as claimed in claim 4, wherein the percentage is about 75 percent.

6. A method as claimed in claim 4, further comprising
   establishing a third interval that extends from the highest peak in the first interval to a fourth point positioned at a distance ahead of the highest peak in the first interval equal to a second percentage of the distance between the highest peak in the first interval and the highest peak in the second interval; and identifying the highest peak of the pressure waveform in the third interval; and modifying the displayed waveform such that the identified highest peak of the pressure waveform in the third interval is distinguished from the highest peak in the first interval, the highest peak in the second interval, and from the rest of the pressure waveform.

7. A method as claimed in claim 6, wherein the second percentage is from about 25 percent to about 50 percent.

8. A method as claimed in claim 2, wherein the offsets of the first and second points are about 150 ms.

9. A method as claimed in claim 2, wherein the offsets of the first and second points are about 100 ms.

10. A method as claimed in claim 2, wherein the offsets of the first and second points are about 75 ms.

11. A method of identifying waves in a pressure waveform, the method comprising:

displaying the waveform on a monitor;

establishing a time reference based on R waves in an ECG;

determining a first interval in the pressure waveform between a first point offset a predetermined amount ahead of a first R wave and a second point offset a predetermined amount behind the first R wave;

identifying the highest peak of the pressure waveform in the first interval;

identifying a second R wave in the ECG subsequent in time to the first R wave;

establishing a second interval that extends from the second point to a third point, the third point positioned at a distance ahead of the second point equal to a first percentage of the interval from the second point to a predetermined amount behind the second R wave;

identifying the highest peak in the pressure waveform in the second interval;

establishing a third interval that extends from the highest peak in the first interval to a fourth point positioned at a distance ahead of the highest peak in the first interval equal to a second percentage of the distance between the highest peak in the first interval and the highest peak in the second interval;

identifying the highest peak in the pressure waveform in the third interval; and modifying the displayed waveform such that the identified highest peaks of the pressure waveform in the first, second, and third intervals are distinguished from each other and the rest of the pressure waveform.

12. A method as claimed in claim 11, wherein the ECG indicates a heart rate, and wherein the offsets of the first and second points are based on the heart rate.

13. A method as claimed in claim 12, wherein the offsets of the first and second points are equal to one another.

14. A method as claimed in claim 11, wherein the first percentage is about 75 percent.

15. A method as claimed in claim 11, wherein the second percentage is from about 25 percent to about 50 percent.

16. A method as claimed in claim 11, wherein the offsets of the first and second points are about 150 ms.

17. A method as claimed in claim 11, wherein the offsets of the first and second points are about 100 ms.

18. A method as claimed in claim 11, wherein the offsets of the first and second points are about 75 ms.

19. A method as claimed in claim 11, wherein the highest peaks in the first, second, and third intervals are distinguished by different colors.

20. A method as claimed in claim 19, wherein the colors are red, green, and blue.

21. A method as claimed in claim 11, wherein the highest peaks in the first, second, and third intervals are distinguished by different markings.

22. A wave identifying system comprising:

an ECG acquisition module;

a pressure waveform acquisition module to acquire a pressure waveform;

an analysis module coupled to the ECG acquisition module and the pressure waveform acquisition module, the analysis module operable to establish a time reference based on R waves in an ECG, determine a first interval in the pressure waveform between a first point offset a predetermined amount ahead of a first R wave and a second point offset a predetermined amount behind the first R wave, identify the highest peak of the pressure waveform in the first interval, identify a second R wave in the ECG subsequent in time to the first R wave, establish a second interval that extends from the second point to a third point, the third point positioned at a distance ahead of the second point equal to a first percentage of the interval from the second point to a predetermined amount behind the second R wave, identify the highest peak in the pressure waveform in the second interval, establish a third interval that extends from the highest peak in the first interval to a fourth point positioned at a distance ahead of the highest peak in the first interval equal to a second percentage of the distance between the highest peak in the first interval and the highest peak in the second interval, identify the highest peak in the pressure waveform in the third interval, and generate an output signal that causes a monitor to display a waveform representing the pressure waveform such that the identified highest peaks of the pressure waveform in the first, second, and third intervals are distinguished from each other and the rest of the displayed waveform; and a display coupled to the analysis module.

23. A system as claimed in claim 22, wherein the output signal of the analysis module causes the displayed waveform to be displayed in a color-coded manner.

24. A method as claimed in claim 12, wherein the offsets of the first and second points are equal to one another.

25. A waveform component identification system comprising:

a physiological waveform acquisition module;

a pressure waveform acquisition module to acquire a pressure waveform;

an analysis module coupled to the physiological waveform acquisition module and the pressure waveform acquisition module; and a monitor coupled to the analysis module, the analysis module operable to determine a plurality of waves in the pressure waveform and generate an output signal including information such that each of the plurality of waves is distinguished from one another when displayed on the monitor.

26. A method of identifying components in a waveform, the method comprising:

displaying a waveform;

identifying a number of waves in a number of intervals of the waveform; and modifying the displayed waveform such that the identified waves are distinguished from each other and the rest of the waveform.

27. A method of analyzing waves in a waveform, the method comprising:
- displaying an ECG waveform;
- displaying a pressure waveform;
- measuring intervals on the pressure waveform; wherein the intervals correlate to the ECG waveform;
- identifying the highest point of each interval; and
- modifying the displayed pressure waveform wherein the highest point of each interval is distinguished from the rest of the pressure waveform.

28. A wave detection system comprising:
- an acquisition system for detecting a first waveform and a second waveform;
- a monitor for displaying the first waveform and the second waveform; wherein the second waveform correlates to the first waveform, and the second waveform is modified to identify waves which are distinguished from each other and the rest of the second waveform.

* * * * *